United States Patent [19]

Quigg

[11] 4,036,699
[45] July 19, 1977

[54] FERMENTATION APPARATUS AND METHOD
[75] Inventor: Donald J. Quigg, Bartlesville, Okla.
[73] Assignee: Phillips Petroleum Company, Bartlesville, Okla.
[21] Appl. No.: 654,436
[22] Filed: Feb. 2, 1976
[51] Int. Cl.² .............................................. C12B 1/14
[52] U.S. Cl. .................................. 195/142; 195/115; 195/143; 195/109
[58] Field of Search ........................ 195/109, 143, 142

[56] References Cited

U.S. PATENT DOCUMENTS

| 2,305,796 | 12/1942 | Seidel | 195/95 X |
|---|---|---|---|
| 3,625,834 | 12/1971 | Muller | 195/109 |
| 3,630,848 | 12/1971 | Le Francois | 195/143 X |
| 3,705,082 | 12/1972 | Hondermarck et al. | 195/142 X |
| 3,717,552 | 2/1973 | Hondermarck et al. | 195/143 X |
| 3,732,148 | 5/1973 | Franckowiak et al. | 195/109 |
| 3,910,826 | 10/1975 | Kataoka | 195/143 X |

Primary Examiner—Raymond N. Jones
Assistant Examiner—Robert J. Warden

[57] ABSTRACT

A fermentation apparatus is provided wherein a vessel has mounted therein a draft tube with an impeller adjacent one end thereof to induce circulation of ferment medium through the draft tube and a flow path defined by portions of the draft tube and the vessel. A plurality of conduits have major portions thereof positioned exteriorly of the vessel with the ends thereof opening into portions of the vessel to provide a flow loop for medium from the vessel. Heat exchange means, pump means and oxygen introduction means are provided in each of the conduits to facilitate the fermentation process. In operation, medium taken from one portion of the vessel is returned to another portion of the vessel in a cooled and oxygen-enriched state.

6 Claims, 2 Drawing Figures

FERMENTATION APPARATUS AND METHOD

Aerobic fermantations of compounds such as alcohols with microorganisms such as bacteria, yeasts or fungi are known to be useful for the production of single cell protein which shows promise as a valuable source of much needed protein in the world. However, such processes have encountered problems in their commercial utilization. One problem is that the economic necessity of utilizing a high productivity fermentation process, i.e., high weight of microbial cells per fermenter volume per hour, and the concurrent necessity for removing large amounts of heat which are produced in the exothermic aerobic fermentation process. Processes capable of high productivity also require a fermentation apparatus capable of high oxygen transfer rates which is necessary to sustain the desired high growth rate for the microorganisms. It has appeared that the utilization of efficient heat transfer means within a fermentation vessel has often been self-defeating in terms of maintaining a high oxygen transfer rate for the fermentation. For example, a fermentation vessel equipped with a large amount of heat transfer surface within a fermentation vessel is often times unsuited for maintaining high oxygen transfer rates in the fermentation process.

Therefore, a principal object of the present invention is to provide an apparatus for conducting fermentation which is simple and provides a means of maintaining a high oxygen transfer rate while at the same time providing effective heat transfer to permit the obtaining of a high productivity aerobic fermentation process for the production of microbial cells. It is a further object of the present invention to provide such a fermentation apparatus of high capacity and thus reduce the number of vessels needed in a typical largescale fermentation plant. A further object of the present invention is to provide such a fermentation apparatus wherein a plurality of external loops are provided to form flow paths between various selected portions of the vessel for varying circulation of ferment from the usual flow path. A further object of the present invention is to provide such a fermentation apparatus wherein a vessel used for conducting fermentation of similar outer dimensions to those of conventional fermentation vessels while having a larger fermentation capacity by reducing the need for heat exchange surface within the interior of the fermentation apparatus. A still further object is to provide a method of conducting fermentation in which ferment is circulated within the vessel in a loop flow path while ferment is withdrawn from the vessel for flow through an external loop and then returned to the vessel.

Other objects and advantages of the present invention will become apparent from the following detailed description taken in connection with the accompanying drawings wherein are set forth by way of illustration and example certain embodiments of the present invention.

Figure 1:
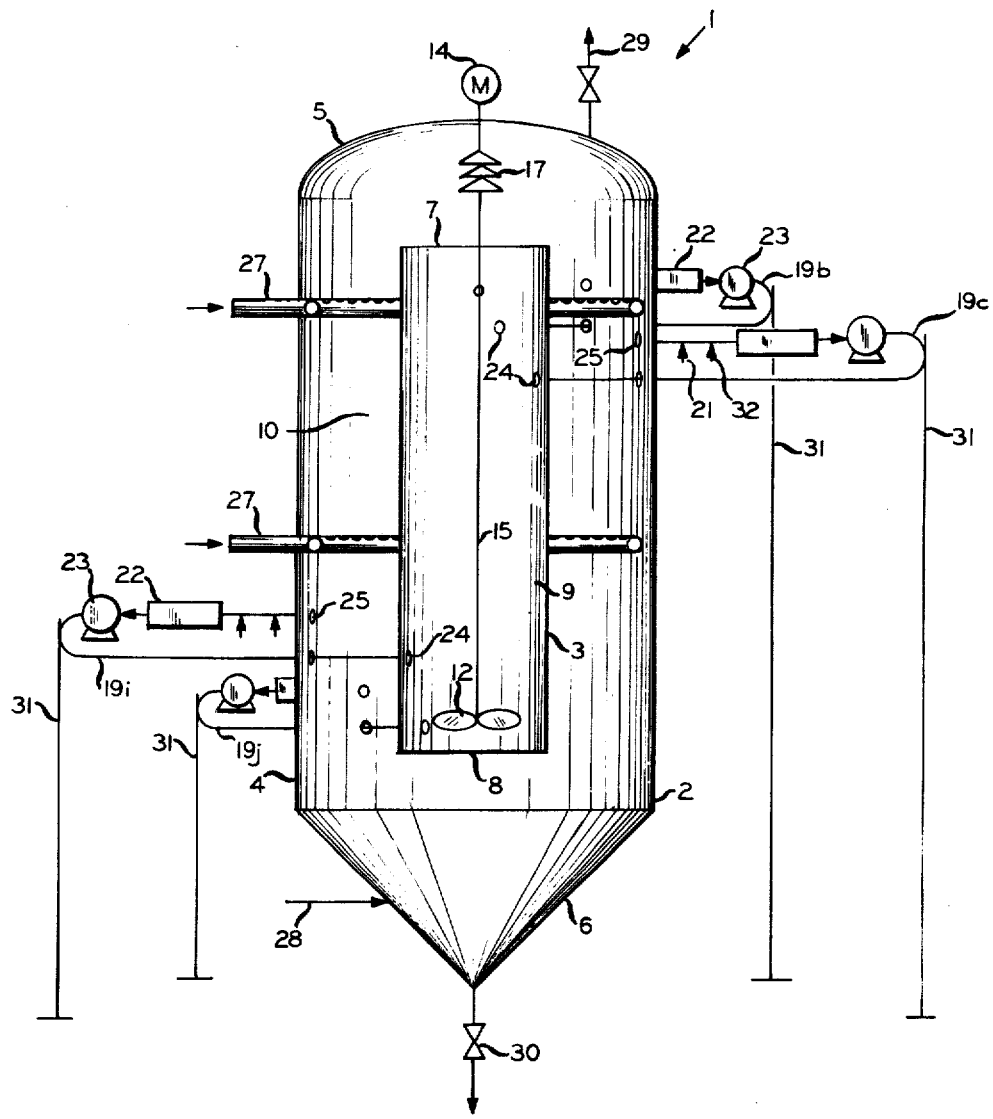
FIG. 1 is a somewhat diagrammatic elevational view of a fermentation apparatus.

Referring more in detail to the drawings:

As required, detailed embodiments of the present invention are disclosed herein, however, it is to be understood that the disclosed embodiments are merely exemplary of the invention which may be embodied in various forms. Therefore, specific structral and functional details disclosed herein are not to be interpreted as limiting but merely as a basis for the claims and as a representative basis for teaching one skilled in the art to variously employ the present invention in virtually any appropriate detailed structure.

The reference numeral 1 designates generally a fermentation apparatus which is comprised of a vessel 2 which has mounted therein a generally centrally located draft tube 3. The vessel 2 can be of any suitable size and shape and, as shown, is generally cylindrical having a side wall 4 and opposite ends 5 and 6. In the illustrated structure the draft tube is generally cylindrically shaped having opposite open ends 7 and 8 with the draft tube 3 defining a flow path 9 therethrough. As shown, the draft tube 3 is spaced from the interior surface of the side wall 2 and forms a flow path 10 therebetween which is annular in shape.

Suitable flow inducing means such as an impeller 12 is provided in the apparatus 1 to induce flow circulation through the flow paths 9 and 10. As shown, the impeller 12 is positioned adjacent the end 8 of the draft tube 3 and is suitably power operated as by being connected to a motor 14 via a shaft 15. Some aerobic fermentation processes will produce a foam and as such it may be desirable to provide a mechanical type foam breaker 17, which is well known in the art, and, as shown, is positioned adjacent the upper end 5 of the vessel 2 and is operable to separate foam into its constituent phases of gas and liquid. The foam breaker 17 can be of any suitable type and can be provided with a central exhaust (not shown) and can be powered by either the motor 14 or separate motive power means.

Figure 2:
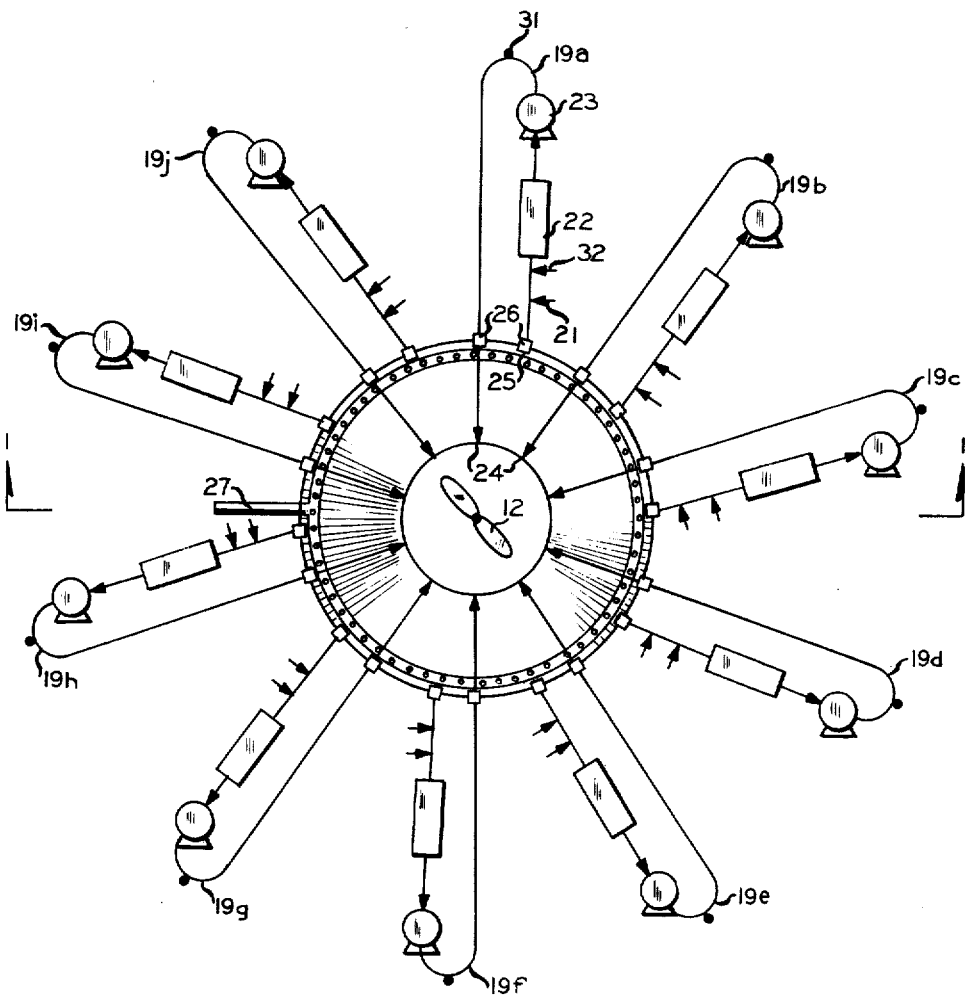
FIG. 2 is a plan view of the fermentation apparatus as shown in FIG. 1.

The apparatus 1 is provided with a plurality of conduits 19 (denoted by $a, b, c, d, e, f, g, h, i$ and $j$ for clarity) each having opposite open ends with one end opening into one of the flow paths 9 or 10 and the other end also opening into one of the flow paths 9 and 10. A major portion of each of the conduits 19 is positioned exteriorly of the vessel 2 and, preferably, each is provided with oxygen introduction means 21 which is operable to introduce oxygen into the interior of the respective conduit. Also provided is heat exchange means 22 which is in heat transfer relation with a respective conduit and is operable to remove heat from medium flowing through the respective conduit. Flow inducing means, such as a pump or impeller 23 which is connected into the respective conduit, communicates with a respective conduit and is operable to provide pumping to induce flow of medium through the conduit between the open ends thereof. As shown, one open end 24 of the conduit 19 opens into the flow path 9 and the opposite open end 25 of the conduit opens into the flow path 10. An example of flow direction is, if medium in the vessel 2 flows upwardly through the flow path 10 and downwardly through the flow path 9, then the inlet would be the open end 25 and the outlet of the conduit 19 would be the open end 24 but it is to be understood that other flow arrangements can be provided. In the form shown, the ends 24 and 25 are circumferentially disposed relative to one another or, in other words, they are circumferentially disposed relative to one another or, in other words, they are circumferentially spaced apart so that fluid taken from one circumferential position is introduced into another circumferential position to help induce good mixing of medium flowing within the flow paths 9 and 10. Also, as best seen in FIG. 2, each of the conduits 19 is positioned at different circumferential positions and height positions along the vessel 2 as for example, same can form a helix arrangement on the exterior of the vessel 2 with the ends 24 and 25 preferably being positioned approximately the same distance from one end of the vessel. Such positioning provides good mixing and helps prevent dead or starved areas and can be used to supply cooled medium to an area that is a hard to cool area or lacking in circulation. It is to be also noted that by having a portion of the conduit 19 extend across the flow path 10, these portions of the conduit act as baffles to further help induce mixing of medium flowing through the flow path 10. Preferably, the conduits 19 have the portions that are positioned exteriorly of the vessel 2 connected to the vessel by easily disconnectable couplings 26. The conduits 19 preferably are in a plurality and can be of a number as, for example, from 2 to 20 and preferably from 4 to 12 and have a volume such that the flow rate of the fermentation medium within the fermentation vessel in the flow path 9 and the flow path 10 should be greater than the flow rate of medium within the conduit loops in order to maintain a more or less uniform flow rate of material throughout the system. The conduits 19 also have supports 31 secured thereto to help support same.

In addition to the above-described parts of the apparatus 1, the vessel 2 can be provided with means for introducing oxygen into the medium contained therein and, as shown, the means can include air sparging rings 27 mounted within the interior of the vessel in various positions as is dictated by the particular fermentation process being conducted. Also, the vessel 2 has an inlet 28 for the introduction of fermentation substrate, e.g., alcohols, nutrients and the like into the vessel which are necessary for the cultivation of the microorganisms. Such nutrients contain an assimilible source of nitrogen and various minerals and vitamins. Also, an outlet 29 communicates with the interior of the vessel 2 and is adapted for permitting removal of exhaust gases such as $CO_2$ from the vessel 2. It is to be noted that the outlet 29 can communicate with the interior of the vessel through the foam breaker 17, if desired. Further, an outlet 30 is shown as communicating with a lower portion of the vessel 2 and is operable for removal of product microorganisms produced within the vessel 2.

The fermentation vessel 2 may also be provided with conventional instruments for following and controlling the fermentation process. Such instrumentation includes devices for the measurement of dissolved oxygen, pressure, pH, substrate concentration, foam buildup, temperature and the like. Such instrumentation may be suitably located in any convenient area within the fermentation vessel.

The present invention is more fully understood by a description of the operation thereof. Fermentation medium, including necessary nutrients and a microbial innoculum, is introduced into the vessel 2, as for example, through the inlet 28 and the conditions of fermentation are maintained within the vessel 2 so as to induce the cultivation of the microorganism therein. Loop flow of medium is induced through the flow paths 9 and 10 by operation of the impeller 12. As the medium flows along the flow paths, a certain portion thereof is withdrawn from the flow paths and induced to flow through the conduits 19 by operation of the pumps 23. While flowing through the conduits, the medium is cooled by virtue of coming into heat transfer relation with the heat exchangers 22 and oxygen is also introduced into the medium by the oxygen injectors 21. It is to be noted that nutrients and other fermentation materials can also be introduced into the conduits 19 by injector means 32, if desired. The cooled and oxygen-enriched medium is discharged from the respective conduits 19 back into the vessel 2 for circulation along the flow paths 9 and 10. If foam is produced during the process, same is separated into its constituent phases by the foam breaker 17 with the gas phase being exhausted through outlet 29. The product produced by the fermentation process is removed through the outlet 30 and is then treated in a conventional manner for recovery of the produced single cell protein.

It is to be understood that while I have illustrated and described certain forms of my invention, it is not to be limited to the specific form or arrangement of parts herein described and shown.

What is claimed and desired to be secured by Letters Patent is:

1. A fermentation apparatus comprising:
  a. a vessel having a chamber therein;
  b. a draft tube mounted in said chamber and having flow openings adjacent opposite ends thereof, said draft tube defining a first flow path therethrough and defining a second flow path between same and portions of said vessel;
  c. first flow inducing means in said vessel for inducing flow of fluid along said first and second flow paths;
  d. a conduit having a major portion thereof positioned exteriorly of said vessel and having a first end opening into one of said first flow path and said second flow path and a second end opening into one of said first flow path and said second flow path forming a third flow path with said first and second ends being circumferentially spaced apart;
  e. heat exchange means positioned exteriorly of the vessel and being in heat transfer relation with said conduit; and
  f. second flow inducing means in communication with said conduit and being operable to induce flow therethrough.

2. The apparatus as set forth in claim 1 wherein:
  a. said first and second ends are each positioned approximately the same distance from one end of the vessel.

3. The apparatus as set forth in claim 2 wherein:
  a. said conduit is in a plurality each having a respective said first heat exchange means in heat transfer relation therewith and second flow inducing means communicating therewith.

4. The apparatus as set forth in claim 3 including:
  a. injector means each communicating with a respective said conduit operable to inject oxygen thereinto.

5. The apparatus as set forth in claim 4 wherein:
  a. said second flow inducing means includes an impeller positioned in said conduit.

6. The apparatus as set forth in claim 1 wherein:
  a. said first end opens into said first flow path and the second end opens into said second flow path.

* * * * *